US008372454B2

(12) United States Patent
Aviram et al.

(10) Patent No.: US 8,372,454 B2
(45) Date of Patent: Feb. 12, 2013

(54) METHODS OF MAKING POMEGRANATE COMPOUNDS FOR THE TREATMENT OF ERECTILE DYSFUNCTION

(75) Inventors: Michael Aviram, Kiriat-Haim (IL); Harley R. Liker, Beverly Hills, CA (US)

(73) Assignee: Pom Wonderful LLC, Los Angeles, CA (US)

( * ) Notice: Subject to any disclaimer, the term of this patent is extended or adjusted under 35 U.S.C. 154(b) by 458 days.

(21) Appl. No.: 12/724,661

(22) Filed: Mar. 16, 2010

(65) Prior Publication Data

US 2010/0173029 A1 Jul. 8, 2010

Related U.S. Application Data

(63) Continuation-in-part of application No. 12/564,878, filed on Sep. 22, 2009, which is a continuation of application No. 11/137,248, filed on May 24, 2005, now Pat. No. 7,611,738, application No. 12/724,661, which is a continuation-in-part of application No.

(Continued)

(51) Int. Cl.
*A61K 36/00* (2006.01)
(52) U.S. Cl. .................. 424/769; 424/725; 424/777
(58) Field of Classification Search .................. None
See application file for complete search history.

(56) References Cited

U.S. PATENT DOCUMENTS

| | | | |
|---|---|---|---|
| 5,162,037 A | 11/1992 | Whitson-Fischman | |
| 5,411,733 A | 5/1995 | Hozumi | |
| 5,433,965 A | 7/1995 | Fischer | |
| 5,624,698 A | 4/1997 | Dake | |
| 5,679,351 A | 10/1997 | Walter | |
| 5,830,887 A | 11/1998 | Kelly | |
| 5,840,308 A | 11/1998 | Jassim et al. | |
| 5,850,032 A | 12/1998 | Wann | |
| 5,891,440 A | 4/1999 | Lansky et al. | |
| 5,945,308 A | 8/1999 | Tang | |
| 5,989,557 A | 11/1999 | Bombardelli et al. | |
| 6,033,692 A | 3/2000 | Chukwu | |
| 6,060,063 A | 5/2000 | Lansky et al. | |
| 6,312,753 B1 | 11/2001 | Kealey et al. | |
| 6,361,807 B1 | 3/2002 | Aviram et al. | |
| 6,375,993 B1 | 4/2002 | Aviram et al. | |
| 6,387,370 B1 | 5/2002 | Yegorova | |
| 6,387,418 B1 | 5/2002 | Aviram | |
| 6,544,581 B1 | 4/2003 | Shrikhande et al. | |
| 6,641,850 B1 | 11/2003 | Aviram | |
| 6,642,277 B1 | 11/2003 | Howard et al. | |
| 6,794,375 B2 | 9/2004 | Sarama | |
| 6,800,292 B1 | 10/2004 | Murad | |
| 6,855,352 B2 | 2/2005 | Shoji | |
| 6,977,089 B1 | 12/2005 | Aviram | |
| 7,611,738 B2 | 11/2009 | Bates | |
| 7,645,469 B2 | 1/2010 | Aviram | |
| 2002/0012710 A1 | 1/2002 | Lansky et al. | |
| 2002/0197341 A1 | 12/2002 | Lansky | |
| 2003/0134006 A1 | 7/2003 | Chukwu | |
| 2004/0009262 A1 | 1/2004 | Chukwu | |
| 2004/0126470 A1 | 7/2004 | Harpaz | |
| 2005/0118312 A1 | 6/2005 | Lansky et al. | |

FOREIGN PATENT DOCUMENTS

| | | | |
|---|---|---|---|
| FR | 2 178 968 | | 3/1973 |
| FR | 2178968 A | * | 1/1974 |
| FR | 2380299 | | 2/1977 |
| JP | 10298094 | | 4/1992 |
| JP | 5320037 | | 5/1992 |
| JP | 9110710 | | 10/1995 |
| JP | 11243911 | | 3/1998 |
| JP | 404124140 | | 10/1998 |
| JP | 2003102431 | | 9/2001 |
| RU | 2088119 | | 9/1995 |
| SU | 1251851 | | 3/1984 |
| SU | 1442167 | | 3/1987 |
| WO | 93/23069 | | 11/1993 |
| WO | 95/22254 | | 8/1996 |
| WO | 98/29129 | | 7/1998 |
| WO | 99/66941 | | 12/1999 |
| WO | 00/56177 | | 9/2000 |
| WO | 0137848 | | 5/2001 |
| WO | 02094303 | | 11/2002 |
| WO | 2006/127832 | | 11/2006 |
| WO | 07/127263 | | 8/2007 |

OTHER PUBLICATIONS

Pantuck, et al., "Pomegranate Juice May Slow Prostate Cancer Growth,".
Albrecht, et al., Pomegranate Extracts Potently Suppress Proliferation, Xenograft Growth, and Invasion of Human.
Eva Lonn MD MSc; Use of Carotid Ultrasound to stratify risk; Can J. Cariol vol. 17 Suppl. A May 2001; pp. 22A-25A.

(Continued)

*Primary Examiner* — Christopher R Tate
*Assistant Examiner* — Randall Winston
(74) *Attorney, Agent, or Firm* — Cotman IP Law Group

(57) ABSTRACT

Various processes for producing an extract containing phytochemicals from pomegranates are disclosed. The processes generally comprise providing pomegranate solids, such as the pericarp, inner membrane and seeds; creating a mixture comprising the pomegranate solids in an aqueous solution; adding enzymes to the mixture in an amount sufficient to at least partially degrade the pomegranate solids; heating the mixture to a temperature that permits the maximum rate of catalysis of the enzyme; maintaining the temperature of the heated mixture for a time sufficient to allow at least partial degradation of the pomegranate solids; and removing residual insoluble solid materials from the mixture. Compositions containing the extract may be used as a food product, beverage, pharmaceutical preparations, nutritional supplements, vitamin supplements, food additives, and food supplements. The compositions may also be used for preventing or ameliorating disease conditions by administering an effective amount of the composition to a subject in need thereof.

11 Claims, 2 Drawing Sheets

Related U.S. Application Data

12/628,053, filed on Nov. 30, 2009, now Pat. No. 8,221,806, which is a continuation of application No. 11/252,842, filed on Oct. 18, 2005, now Pat. No. 7,645,469, which is a continuation of application No. 10/701,918, filed on Nov. 4, 2003, now Pat. No. 6,977,089, which is a continuation of application No. 09/998,883, filed on Nov. 19, 2001, now Pat. No. 6,641,850, which is a continuation-in-part of application No. 09/294,307, filed on Apr. 19, 1999, now Pat. No. 6,387,418.

OTHER PUBLICATIONS

Mehmet S. Ulgen, MD: The Relationship of Coronary Artery Disease and Carotid Doppler Flow Velocity and Resistance Index in Patients with no Significant Carotid Stenosis; Angiology vol. 52, No. 6, 2001; pp. 433-434.
John R. Crouse III, MD; Predictive Value of Carotid 2-Dimensional Ultrasound, The American Journal of Cardiology; vol. 88 (2A) Jul. 19, 2001; pp. 27E-30E.
D. Ropers et al.; Correlation Between Calcification of the Carotid Arteries Documented by Ultrasound, Coronary Calcifications in Electron-Beam Tomography, and Angiographic Coronary Artery Disease; A Symposium: First International SAI Meeting; p. 85E.
Nicolas Denarie, MD: Difference in Carotid Artery Wall Structure Between Swedish and French Men at Low and High Coronary Risk; Stroke, Aug. 2001; pp. 1775-1779.
Tommi Vasankari et al.; Oxidized LDL and Thickness of Carotid Intima-Media are Associated With Coronary Atherosclerosis in Middle-Aged Men: Lower Levels of Oxidized LDL With Statin Therapy; Atherosclerosis 55 (2001); pp. 403-412.
Olli T. Raitakari et al.; Reduced Myocardial Flow Reserve Relates to Increased Carotid Intima-Media Thickness in Healthy Young Men; Atherosclerosis 156 (2001); pp. 469-475.
Ward A. Riley, PhD; Reproductivity of Noninvasis Ultrasonic Measurement of Carotid Atherosclerosis The Asymptomatic Carotid Artery Plaque Study; Stroke vol. 23; No. 8, Aug. 1992; pp. 1062-1068.
Michiel L. Bots, MD, PhD; Common Carotid Intima-Media Thickness and Risk of Stroke and Myocardial Infarction; Circulation. 1997;96:1432-1437.
Daniel H. O'Leary, MD: Carotid-Artery Intima and Media Thickness as a Risk Factor for Myocardial Infarction and Stroke in Older Adults; The New England Journal of Medicine; Jan. 7, 1999; pp. 14-22.
Frank Tietze; Enzymatic Method of Quantitative Determination of Nanogram Amounts of Total and Oxidized Glutathione: Applications to Mammalian Blood and Other Tissues; Analytical Biochemistry 27, 502-522 (1969).
Mira Rosenblat et al.; Macrophage Glutathione Content and Glutathione Peroxidase Activity Are Inversely Related to Cell-Mediated Oxidation of LDL: In Vitro and In Vivo Studies; Free Radical Biology & Medicine, vol. 24, No. 2, pp. 305-317, 1998.
Cam Patterson et al.; The Oxidation Paradox Another Piece in the Puzzle; Circ. Res. 2000; 87:1074-1076.
Tina Rissanen et al.; Low Plasma Lycopene Concentration is Associated With Increased Intima-Media Thickness of the Carotid Artery Wall; Arterioscler Thromb Vase Biol. Dec. 2000; pp. 2677-2681.
Johannes Hulthe at al.; Antibodies to Oxidized LDL in Relation to Intima-Media Thickness in Carotid and Femoral Arteries in 58-Year-Old Subjectively Clinically Healthy Men; Arterioscler Thromb Vase Biol. pp. 101-107.
Alexandra Levy et al.; Enhanced In Vitro Oxidation of Plasma Lipoproteins Derived From Hypercholesterolemic Patients; Metabolism, vol. 40, No. 8 (Aug. 1991): pp. 794-799.
Hermann Esterbauer et al.; Biochemical, Structural, and Functional Properties of Oxidized Low-Density Lipoprotein; Chemical Research in Toxicology, vol. 3, No. 2, Mar./Apr. 1990 pp. 77-92.
Michael Aviram et al.; Lesioned Low Density Lipoprotein in a Therosclerotic Apotipoprotein E-Deficient Transgenic Mice and in Humans is Oxidized and Aggregated; Biochemical and Biophysical Research Communications, vol. 216, No. 2, 1995, pp. 501-513.

Jane McElveen et al.; Distribution of Paraoxon Hydrolytic Activity in the Serum of Patients after Myocardial Infarction, Clinical Chemistry, vol. 32, No. 4, 1986, pp. 671-673.
Michael I. Mackness et al.; Serum Paraoxonase Activity in Familial Hypercholesterolaemia and Insulin-Dependent Diabetes Mellitus; Atherosclerosis, 86 (1991) pp. 193-199.
Michael Aviram et al.; Human Paroxonase (PON 1) is Inactivated by Oxidized Low Density Lipoprotein and Preserved by Antioxidants; Free Radical Biology & Medicine, vol. 26, Nos. 7/8, 1999 pp. 892-904.
Michael Aviram et al.; Pomegranate Juice Consumption Inhibits Serum Angiotensin Converting Enzyme Activity and Reduces Systolic Blood Pressure; Atherosclerosis 158 (2001) pp. 195-198.
Kitiyakara et al.; Current Opinion in Nephrology and Hypertension; 1998 Lippincott Williams & Wilkins, Inc., vol. 7(5) pp. 531-538.
Eva M. Lonn et al.; Effects of Ramipril and Vitamin E on Atherosclerosis the Study of Evaluate Carotid Ultrasound Changes in Patients Treated With Ramipril and Vitamin E (SECURE); 2001 American Heart Association, Inc. pp. 919-925.
Ping Sun et al.; Blood Pressure, LDL Cholesterol, and Intima-Media Thickness A Test of the "Response to Injury" Hypothesis of Atheroselerosis; Arterioscier Thromb Vase. Biol. 2000 American Heart Association, Inc. pp. 2005-2010.
Caroline A. Abbott et al., Serum Paraoxonase Activity, Concentration, and Phenotype Distribution in Diabetes Mellitus and Its Relationship to Serum Lipids and Lipoproteins; Arterioscierosis, Thrombosis, and Vascular Biology, 1995;15:1812-1818; 1995 American Heart Association, Inc.
Michael G L Hertog et al.; Dietary Antioxidant Flavonoids and Risk of Coronary Heart Disease: the Zutphen Elderly Study; The Lancet, vol. 342, Oct. 23, 1993, pp. 1007-1011.
Irit Maor et al.; Plasma LDL Oxidation Leads to its Aggregation in the Atherosclerotic Apolipoprotein E-Deficient Mice; Arteriosclerosis, Thrombosis, and Vascular Biology. 1997;17:2985-3005, 1997 American Heart Association, Inc.
2003-103614, DW, Dec. 3, 2002, Lansky.
Malik Arshi et al. "Pomegrante fruit juice for chemoprevention and chemotherapy of prostate cancer," Poceedings of the National Academy of Sciences of USA, vol. 102, No. 41, Oct. 11, 2005; pp. 14813-14818.
Aviram et al. "Pomegranate juice consumption reduces oxidative stress, atherogenic modifications to LDL, and platelet aggregation: Studies in humans and in atherosclerotic apolipoprotein E-deficient mice" American Journal of Clinical Nutrition 200005 US, vol. 71, No. 5, May 2000, pp. 1062-1076.
Malik Arshi et al. "Prostate cancer prevention through pomegranate fruit," Cell Cycle, Feb. 2006, vol. 5, No. 4, Feb. 2006, pp. 371-373.
Pantuck A. J. et al. "831. Phase II study of pomegranate juice for men with rising PSA following surgery or radiation for prostate cancer," Journal of Urology, Lippincott Williams & Wilkins, Baltimore, MD, US, vol. 17, No. 4, Suppl. S, Apr. 1, 2005, pp. 225-226.
Kim Nam Deuk et al. "Chemopreventive and adjuvant therapeutic potential of pomegranate (*Punica granatum*) for human breast cancer," Breast Cancer Research and Treatment, vol. 71, No. 3, Feb. 2002, pp. 203-217.
Pantuck A J. eta l. "Phase II study of pomegranate juice for men with rising prostate-specific antigen following surgery or radiation for prostate cancer," Clinical Cancer Research 20060701, vol. 12, No. 13, Jul. 1, 2006, pp. 4016-4026.
Supplementary European Search Report for EP Application No. EP 07 75 8047, mailed on Jan. 29, 2010, 9 pages.
Albrecht, et al., "Pomegranate Extracts Potently Suppress Proliferation, Xenograft Growth, and Invasion of Human Prostate Cancer Cells," European Urology Supplements, vol. 2, Issue 6, 24-27 p. 138 (Sep. 2003).
Seeram, et al., "In vitro antiproliferative, apoptotic and antioxidant activities of punicalagin, ellagic acid and a total pomegranate tannin extract are enhanced in combination with other polyphenols as found in pomegranate juice," Journal of Nutritional Biochemistry, 16(6) pp. 360-367 (2005).
Aviram et al. Atherosclerosis. 2001. vol. 158, pp. 195-198.
Glozman et al. Khim.-Farm. Zh. vol. 23, No. 9, pp. 1111-1115—English translation enclosed, 1989.

Dorlands Medical Dictionary, 27th ed. p. 137, 1988.
Glozman et al. Khim.-Farm. Zh. vol. 23, No. 9, pp. 1111-1115, abstract enclosed, 1989.
Gob et al. Proc. 5th Asian Symp. Med. Plants Spices, Aug. 20-24, 5 pages, abstract enclosed, 1984.
Pereira et al. Ciencia e Clutura, vol. 49, No. 5-6, pp. 354-358, abstract enclosed, 1997.
Singh, Y. J. Ethnopharmacol. vol. 15, No. 1, pp. 57-88, abstract enclosed, 1986.
Batra et al. Acta Pharma. Jugosl. vol. 36, No. 1, pp. 63-66, abstract enclosed, 1986.
[Search Report] PCT/US/00/06758; Int.l Filing Date: Mar. 15, 2000.
[Search Report] PCT/US/00/06758; Int'l. filing Date: Mar. 15, 2000.
Journal of Ethno-Pharmacology 66 (1999) 66, pp. 11-17, Schubert et al.
Food Science and Technology International (1998) 4, pp. 99-105, Zafrilla et al.
International Product Alert bulletin. Dec. 15, 1997. Rubyan Persia Pomegranate Concentrate Extract. PROMT Database. Full text abstract, 1 p.
Kathy K. Griendling, Ph.D. et al.; Oxidate Stress and Cardiovascular Disease; 1997 American Heart Association, Inc.; pp. 3264-3265.
Judith A. Berliner, Ph.D. et al.; Atherosclerosis: Basic Mechanisms, Circulation 91 (9): 2488; pp. 1-26.
Aldons J. Lusis; Atherosclerosis; Insight Review Articles; pp. 233-241.
Michael Aviram; Review of Human Studies on Oxidative Damage and Antioxidant Protection Related to Cardiovascular Diseases; 2000 OPA; pp. 85-97.
Bianca Fuhrman et al.; Flavonoids Protect LDL from Oxidation and Attenuate Atherosclerosis, 2001 Lippincott Williams & Wilkins; pp. 41-48.
L. Iuliano, MD et al.; Radiolabeled Native Low-Density Lipoprotein Injected Into Patients With Carotid Stenosis Accumulates in Macrophages of Atherosclerotic Plaque Effect of Vitamin E Supplementation; Circulation Mar. 21, 2000, American Heart Association; pp. 1249-1254.
Michael Aviram et al.; Pareoxonase Inhibits High-density Lipoprotein Oxidation and Preserves its Functions; The American Society for Clinical Investigation, Inc. vol. 101, No. 8, Apr. 1998. pp. 1581-1590.
Mohamad Navab et al.; The Yin and Yang of Oxidation in the Development of the Fatty Streak; 1996 American Heart Association: 16:831-842; pp. 1-24.
Michael Aviram et al.; Human Serum Paraxonoases (PON1) Q and R Selectively Decrease Lipid Peroxides in Human Coronary and Carotid Atherosclerotic Lesions PON1 Esterase and Peroxidase-Like Activities, 2000 American Heart Associations, Inc.; pp. 2610-2517.
Michael I. Mackness et al.; Protection of Low-density Lipoprotein Against Oxidative Modification by High-density Lipoprotein Associated Paraoxonase; Atherosclerosis 104 (1993) pp. 129-135.
Patricia Langley; Why a Pomegranate?; BMJ Volum 321; Nov. 4, 2000; pp. 1153-1154.
Maria I. Gil et al.; Antioxidant Activity of Pomegranate Juice and its Relationship with Phenolic Composition and Processing; J. Agric. Food Chem. 2000, 48, pp. 4581-4589.
Michael Aviram et al.; Pomegranate Juice Consumption Reduces Oxidative Stress, Atherogenic Modifications to LDL, and Platelet Aggregation: Studies in Humans and in AtherMichael Aviram; Plasma Lipoprotein Separation by Discontinuous Density Gradient Ultracentrifugation in Hyperlipoproteinemic Patients; Biochemical Medicine, vol. 30, No. 1, Aug. 1983; pp. 111-118, osclerotic Apolipoprotein E-deficient Mice; The American Journal of Clinical Nutrition; May 2000 vol. 71 No. 5; pp. 1062-1076.
Michael Aviram; Plasma Lipoprotein Separation by Discontinuous Density Gradient Ultracentrifugation in Hyperlipoproteinemic Patients; Biochemical Medicine, vol. 30, No. 1, Aug. 1983; pp. 111-118.
Oliver H. Lowry et al.; Protein Measurement With the Folin Phenol Reagent; Department of Pharmacology, Washington University School of Medicine; May 28, 1951; pp. 265-275.
John A. Buege et al.; Microsomal Lipid Peroxidation; Microsomal Electron Transport and Cyt. P-450; pp. 302-310.

H. Esterbauer et al., Continuous Monitoring of In Vitro Oxidation of Human Low Density Lipoprotein; Free Rad. Res. Comms. vol. 6, No. 1, pp. 67-76.
M. El-Saadani et al.; A spectrophotometric Assay for Lipid Peroxides in Serum Lipoproteins Using a Commercially Available Reagent; Journal of Lipid Research, vol. 30, 1989; pp. 627-630.
John C. Khoo et al.; Enhanced Macrophage Uptake of Low Density Lipoprotein After Self-Aggregation; Jul./Aug. 1988; Arteriosclerosis 8:348-358.
Chris H.A. van de Lest et al.; A Spectrophotometric Method for the Determination of Heparan Sulfate; Biochimica et Biophysicia Acta 1201 (1994) pp. 305-311.
Gerd Assmann; Quantification of High-Density-Lipoprotein Cholesterol by Precipitation with Phosphotungstic Acid/$MgCl_2$ ; Clin. Chem. 29/12, pp. 2026-2030 (1983).
Barry J. Kitchen et al. Effects of Lipid Removal on the Molecular Size and Kinetic Properties of Bovine Plasma Arylesterase; Biochem. J. (1973) 135, pp. 93-99.
G. Geroulakos et al.; Arterial Wall Changes in Type 2 Diabetic Subjects; pp. 692-695.
Martin G. Veller et al., Measurement ef the Ultrasonic Intima-Media Complex Thickness in Normal Subjects; Journal of Vascular Surgery, Apr. 1993; pp. 719-725.
Marielle Kaplan et al.; Pomegranate Juice Supplementation to Atherosclerotic Mice Reduces Macrophage Lipid Peroxidation, Cellular Cholesterol Accumulation and Development of Atherosclerosis; The Journal of Nutrition, vol. 131, No. 8, Aug. 2001; pp. 2082-2089.
C. Ben Nasr et al.; Quantitative Determination of the Polyphenolic Content of Pomegranate Peel; Z. Lebensm Unters Forsch (1906) 203: pp. 374-378.
T. Mudrikova et al.; Carotid Intima-media Thickness in Relation to Macrovascular Disease in Patients With Type 2 Diabetes Mellitus, National Library of Medicine; Wien Klin Wochenschr Oct. 27, 2000; 112 (20):887-91.
Toshiyuki Uehara et al.; MR Angiographic Evaluation of Carotid and Intracranial Arteries in Japanese Patients Scheduled for Coronary Artery Bypass Grafting; Cerebrovascular Diseases 2001;11:341-345.
Seeram et al. "Bioavailability of ellagic acid in human plasma after consumption of ellagitannins from pomegranate (*Punica granatum* L.) juice", Clinica Chimica Acta 348 (2004) 63-68.
Seeram, et al., "Pomegranate Juice Ellagitannin Metabolites Are Present in Human Plasma and Some Persist in Urine for Up to 48 Hours", Journal of Nutrition, 2006, 2481-2485.
Seeram, et al. "Pomegranate Juice and Extracts Provide Similar Levels of Plasma and Urinary Ellagitannin Metabolites in Human Subjects" Journal of Medicinal Food, 11 (2)2008, 390-394.
D. Syed, et al. "Photochemopreventive Effect of Pomegranate Fruit Extract on UVA-mediated Activation of Cellular Pathways in Normal Human Epidermal Keratinocytes" Photochemistry and Photobiology, 2006, 82: 398-405.
Adams, et al. "Pomegranate Juice, Total Pomegranate Ellagitannins, and Punicalagin Suppress Inflammatory Cell Signaling in Colon Cancer Cells" Journal of Agricultural and Food Chemistry, 2006, 54, 980-985.
V. Adhami, et al. "Polyphenols from green tea and pomegranate for prevention of prostate cancer" Free Radical Research, Oct. 2006; 40(10): 1095-1104.
S. Kasimsetty, et al. "Effects of Pomegranate Chemical Constituents/ Intestinal Microbial Metabolites on CYP1B1 in 22Rv1 Prostate Cancer Cells" Journal of Agriculture and Food Chemistry, 2009, 57, 10636-10644.
Sartippour, et al., "Ellagitannin-rich pomegranate extract inhibits angiogenesis in prostate cancer in vitro and in vivo" International Journal of Oncology, 2008, 32:475-480.
Rettig, et al. "Pomegranate extract inhibits androgen-independent prostate cancer growth through a nuclear factor-KB-dependent mechanism" Molecular Cancer Therapy, 2008; 7(9): 2662-71.
Seeram, et al."Pomegranate Ellagitannin-Derived Metabolites Inhibit Prostate Cancer Growth and Localize to the Mouse Prostate Gland" Journal of Agricultural and Food Chemistry, 2007, 55, 7732-7737.

Hong, et al. "Pomegranate polyphenols down-regulate expression of androgen-synthesizing genes in human prostate cancer cells overexpressing the androgen receptor" Journal of Nutritional Biochemistry, 2008, 8 pages.

J. Trombold, et al. "Ellagitannin Consumption Improves Strength Recovery 2-3 d after Eccentric Exercise" The American College of Sports Medicine, 2010, 493-498.

B. Fuhrman, et al. "Pomegranate juice polyphenols increase recombinant paraoxonase-1 binding to high-density lipoprotein: Studies in vitro and in diabetic patients" Nutrition 26 (2010) 359-366.

J. Khateeb, et al. "Paraoxonase 1 (PON1) expression in hepatocytes is upregulated by pomegranate polyphenols: A role for PPAR" Atherosclerosis, 2009, 7 pages.

M. Davidson, et al. "Effects of Consumption of Pomegranate Juice on Carotid Intima-Media Thickness in Men and Women at Moderate Risk for Coronary Heart Disease" American Journal of Cardiology, 2009, 936-942.

O. Rozenberg, et al. Pomegranate juice sugar fraction reduces macrophage oxidative state, whereas white grape juice sugar fraction increases it Atherosclerosis, 188 (2006) 68-76.

Mattiello, et al. "Effects of Pomegranate Juice and Extract Polyphenols on Platelet Function" Journal of Medicinal Food, 12 (2) 2009, 7 pages.

Sumner, et al. "Effects of Pomegranate Juice Consumption on Myocardial Perfusion in Patients With Coronary Heart Disease" American Journal of Cardiology, 2005, 5 pages.

M. Aviram, et al. "Pomegranate Phenolics from the Peels, Arils, and Flowers Are Antiatherogenic: Studies in Vivo in Atherosclerotic Apolipoprotein E-Deficient (E0) Mice and in Vitro in Cultured Macrophages and Lipoproteins" Journal of Agricultural and Food Chemistry, 2008, 56, 1148-1157.

Shiner et al. "Macrophage paraoxonase 2 (PON2) expression is up-regulated by pomegranate juice phenolic anti-oxidants via PPAR and AP-1 pathway activation" Atherosclerosis, 2007, 9 pages.

de Nigris, et al. "Effects of a Pomegranate Fruit Extract rich in punicalagin on oxidation-sensitive genes and eNOS activity at sites of perturbed shear stress and atherogenesis" Cardiovascular Research, 2007, 73, 414-423.

de Nigris, et al. "Pomegranate juice reduces oxidized low-density lipoprotein downregulation of endothelial nitric oxide synthase in human coronary endothelial cells" Nitric oxide, 2006 15 259-263.

L. Ignarro, et al. "Pomegranate juice protects nitric oxide against oxidative destruction and enhances the biological actions of nitric oxide" Nitric oxide, 2006, 15, 93-102.

de Nigris et al. "Beneficial effects of pomegranate juice on oxidation-sensitive genes and endothelial nitric oxide synthase activity at sites of perturbed shear stress" Proceedings of the National Academy of Sciences, 2005, vol. 102, No. 13, 6 pages.

Rosenblat, et al. "Pomegranate Byproduct Administration to Apolipoprotein E-Deficient Mice Attenuates Atherosclerosis Development as a Result of Decreased Macrophage Oxidative Stress and Reduced Cellular Uptake of Oxidized Low-Density Lipoprotein" Journal of Agricultural and Food Chemistry, 2006, 54, 1928-1935.

de Nigris, et al. "The influence of pomegranate fruit extract in comparison to regular pomegranate juice and seed oil on nitric oxide and arterial function in obese Zucker rats" Nitric Oxide, 2007 17, 50-54.

Fuhrman, et al. "Pomegranate juice inhibits oxidized LDL uptake and cholesterol biosynthesis in macrophages" Journal of Nutritional Biochemistry, 2005, 16, 570-576.

Kaplan, et al. "Pomegranate Juice Supplementation to Atherosclerotic Mice Reduces Macrophage Lipid Peroxidation, Cellular Cholesterol Accumulation and Development of Atherosclerosis" Journal of Nutrition, 2001, 2082-2089.

M. Aviram, et al. "Pomegranate juice consumption for 3 years by patients with carotid artery stenosis reduces common carotid intima-media thickness, blood pressure and LDL oxidation" Clinical Nutrition, 2004, 23, 423-433.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007, 83: 882-888.

Lorean et al. "Maternal Dietary Supplementation with Pomegranate Juice is Neuroprotective in an Animal Model of Neonatal Hypoxic-Ischemic Brain Injury" Pediatric Research, 2005, vol. 57, No. 6, 7 pages.

Shah, et al. "Pomegranate juice decreases amyloid load and improves behavior in a mouse model of Alzheimer's disease" Neurobiology of Disease, 2006, Abstract.

D. Bialonska, et al. "Urolithins, Intestinal Microbial Metabolites of Pomegranate Ellagitannins, Exhibit Potent Antioxidant Activity in a Cell-Based Assay" Journal of Agriculture and Food Chemistry, 2009, 57, 10181-10186.

Y. Zhang, et al. "Absence of Pomegranate Ellagitannins in the Majority of Commercial Pomegranate Extracts: Implications for Standardization and Quality Control" Journal of Agricultural and Food Chemistry, 2009, 57, 7395-7400.

Y. Zhang, et al. "International Multidimensional Authenticity Specification (IMAS) Algorithm for Detection of Commercial Pomegranate Juice Adulteration", Journal of Agricultural and Food Chemistry, 2009, 9 pages.

S. Madrigal-Carballo, et al. "Pomegranate (*Punica granatum*) supplements: authenticity, antioxidant and polyphenol composition" Journal of Functional Foods, 2009, 6 pages.

K. Martin et al. "Development of a novel pomegranate standard and new method for the quantitative measurement of pomegranate polyphenols" Journal of Science of Food and Agriculture, 2009; 89:157-162.

N. Seeram, et al. "Comparison of Antioxidant Potency of Commonly Consumed Polyphenol-Rich Beverages in the United States" Journal of Agricultural and Food Chemistry, 2008, 56, 1415-1422.

Gil et al. "Antioxidant Activity of Pomegranate Juice and Its Relationship with Phenolic Composition and Processing" Journal of Agricultural and Food Chemistry, 2000, 48, 4581-4589.

Rosenblat, et al. "Consumption of polyphenolic-rich beverages (mostly pomegranate and black currant juices) by healthy subjects for a short term increased serum antioxidant status, and the serum's ability to attenuate macrophage cholesterol accumulation" Food & Function, 2010, 1, 99-109.

G. Borges, et al. "Comparison of the polyphenolic composition and antioxidant activity of European commercial fruit juices" Food & Function, 2010, 11 pages.

A. Sundararajana, et al. "Influenza virus variation in susceptibility to inactivation by pomegranate polyphenols is determined by envelope glycoproteins" Elsevier, 2010 (1-9).

R. Oliveira, et al. "Effects of feeding polyphenols from pomegranate extract on health, growth, nutrient digestion, and immunocompetence of calves" American Dairy Science Association, 2010, 93:4280-4291.

M. Haidari, et al. "Pomegranate(*Punica granatum*) purified polyphenol extract inhibits influenza virus and has a synergistic effect with oseltamivir" Phytomedicine, 2009, 10 pages.

D. Bialonska, et al. "The influence of pomegranate by-product and punicalagins on selected groups of human intestinal microbiota" International Journal of Food Microbiology, 140 (2010) 175-182.

M. Reddy, et al. "Antioxidant, Antimalarial and Antimicrobial Activities of Tannin-Rich Fractions, Ellagitannins and Phenolic Acids from *Punica granatum* L." Planta Medica, 2007, 7 pages.

M. Shukla, et al. "Consumption of hydrolyzable tannins-rich pomegranate extract suppresses inflammation and joint damage in rheumatoid arthritis" Nutrition, 24, 2008, 733-743.

Z. Rasheed, et al. "Polyphenol-rich pomegranate fruit extract (POMx) suppresses PMACI-induced expression of pro-inflammatory cytokines by inhibiting the activation of MAP Kinases and NF-κB in human KU812 cells" Journal of Inflammation, 2009, 12 pgs.

Glycaemic Index Research Service "A Study to Measure the Glycaemic Index Value of Pomegranate Juice" The School of Molecular and Microbial Bio-sciences at Sydney University, Mar. 2009, 22 pgs.

B. McFarlin, et al. "Pomegranate seed oil consumption during a period of high-fat feeding reduces weight gain and reduces type 2 diabetes risk in CD-1 mice" British Journal of Nutrition, 2008, 6 pages.

W. Rock, et al. "Consumption of Wonderful Variety Pomegranate Juice and Extract by Diabetic Patients Increases Paraoxonase 1 Association with High-Density Lipoprotein and Stimulates Its Catalytic Activities" Journal of Agricultural and Food Chemistry, 2008, 56, 8704-8713.

M. Rosenblat, et al. "Anti-oxidative effects of pomegranate juice (PJ) consumption by diabetic patients on serum and on macrophages" Atherosclerosis, 187 (2006) 363-371.

Q. Zhang, et al. "Dietary antioxidants improve arteriogenic erectile dysfunction" International Journal of Andrology, 33, 2010, 1-11.

K. Azadzoi, et al."Oxidative Stress in Arteriogenic Erectile Dysfunction: Prophylactic Role of Antioxidants" Journal of Urology, 2005, vol. 174, 386-393.

Forest, et al. "Efficacy and safety of pomegranate juice on improvement of erectile dysfunction in male patients with mild to moderate erectile dysfunction: a randomized, placebo-controlled, double-blind, crossover study" International Journal of Impotence Research, 2007, 1-4.

S. Strum, et al. "Pomegranates and Prostate Health: A Research Report", PCRI Insights, 2008, vol. 11: No. 3, 36 pages.

A. McCutcheon, et al. "Scientific and Clinical Monograph for POM Wonderful Pomegranate Juice" American Botanical Council, 2008, 20 pgs.

M. Aviram, et al. "Pomegranate juice flavonoids inhibit low-density lipoprotein oxidation and cardiovascular diseases: Studies in atherosclerotic mice and in humans" Drugs Under Experimental and Clinical Research XXVIII, 2003, 15 pages.

M. Warren, et al. "Pomegranate's Ancient Roots to Modern Medicine, Pomegranates: Ancient Roots to Modern Medicine" Taylor and Francis, 2006, 158-166.

D. Heber, et al. "Safety and Antioxidant Activity of a Pomegranate Ellagitannin-Enriched Polyphenol Dietary Supplement in Overweight Individuals with Increased Waist Size" Journal of Agricultural and Food Chemistry, 2007, 55, 10050-10054.

D. Farkas, et al. "Pomegranate Juice Does Not Impair Clearance of Oral or Intravenous Midazolam, a Probe for Cytochrome P450-3A Activity: Comparison With Grapefruit Juice" Journal of Clinical Pharmacology, 2007; 47;286-294.

F. Afaq, et al. "Protective effect of pomegranate-derived products on UVB-mediated damage in human reconstituted skin" Experimental Dermatology, 2009.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007.

D Pérez et al., Wine, Diet, Antioxidant Defenses and Oxidative Damage. Annals of the New York Academy of Sciences (2002),957:136-145.

KJ Joshipura, et al., The Effect of Fruit and Vegetable Intake on Risk for Coronary Heart Disease. Annals of Internal Medicine (2001),134:1106-1114.

http://www.wonderfulpomegranateresearch.com/featured.

* cited by examiner

METHODS OF MAKING POMEGRANATE COMPOUNDS FOR THE TREATMENT OF ERECTILE DYSFUNCTION

CROSS REFERENCE TO RELATED APPLICATIONS

This application is a Continuation-in-part of prior filed and co-pending U.S. patent application Ser. No. 12/564,878, filed Sep. 22, 2009 with a priority date of May 24, 2005 and entitled "Process for Extracting Phytochemicals from Pomegranate Solids and Compositions and Methods of Use Thereof" (the '878 application), which is a Continuation of U.S. patent application Ser. No. 11/137,248 filed May 24, 2005, now U.S. Pat. No. 7,611,738 (the '738 patent). Both the '878 application and '738 patent are hereby incorporated by reference in their entirety. This application is also a Continuation-in-part of U.S. application Ser. No. 12/628,053, filed Nov. 30, 2009 now U.S. Pat. No. 8,221,806 and entitled "Methods of Using Pomegranate Extracts for Causing Regression in Lesions Due to Arteriosclerosis in Humans" (the '053 application), which is a Continuation of application Ser. No. 11/252,842, filed Oct. 18, 2005, now U.S. Pat. No. 7,645,469, (the '469 patent), which is a Continuation of application Ser. No. 10/701,918, filed Nov. 4, 2003, now U.S. Pat. No. 6,977,089 (the '089 patent), which is a Continuation of application Ser. No. 09/998,883, filed on Nov. 19, 2001, now U.S. Pat. No. 6,641,850 (the '850 patent), which is a Continuation-in-part of application Ser. No. 09/294,307, filed on Apr. 19, 1999, and entitled "Pomegranate Extracts and Methods of Use Thereof", now U.S. Pat. No. 6,387,418 (the '418 patent). The '053 application, '469 patent, '089 patent, '850 patent, and '418 patent are hereby incorporated by reference in their entirety.

BACKGROUND OF THE INVENTION

1. Field of the Invention

The present invention relates generally to pomegranate compounds, and more particularly, to methods for obtaining and using extracts from pomegranate solids and compositions comprising pomegranate extracts and pomegranate juice to treat arteriogenic erectile dysfunction.

2. Description of the Related Art

Oxidative stress, a major contributor to cardiovascular diseases, is associated with lipid peroxidation in arterial macrophages and in lipoproteins. Oxidized low-density lipoprotein (Ox-LDL) was shown to be atherogenic, thus, interventions to inhibit LDL oxidation by dietary antioxidants is of major importance to attenuate atherosclerosis. It was recently shown that vitamin E supplementation to subjects with carotid artery stenosis inhibited LDL accumulation in arterial macrophages. Protection of lipids from oxidation can be also achieved by serum paraoxonase (PON1), an HDL-associated esterase that can hydrolyze and reduce specific lipid peroxides in arterial cells and lipoproteins in coronary and carotid lesions.

Vascular risk factors, including hypercholesterolemia, atherosclerosis, hypertension and diabetes mellitus, can interfere with the intricate neurovascular mechanisms underlying normal erection. Hypoxemia, sleep apnea and respiratory failure are also increasingly recognized as causes of erectile dysfunction (ED). These conditions are known to induce oxidative tissue injury due to accumulation of reactive oxygen species (ROS) such as superoxide, $H_2O_2$ and hydroxyl radicals.

It is well-known that fruits and vegetables are an essential part of a healthy diet. Chief, among the reasons, is that fruits and vegetables are rich sources of important phytochemicals, which provide essential nutrients and enhance the body's ability to prevent and fight disease. There is a multitude of phytochemicals, in unique combinations, in different fruits and vegetables, and each function differently in the body: as anti-oxidants, as anti-allergenic, as anti-carcinogenic, as anti-inflammatory, as anti-viral, and/or anti-proliferative.

There are many kinds of antioxidants, some produced by the body and others derived from the foods we eat. When the body's natural antioxidant defenses are lowered or greater amounts of free radicals are being produced, the body becomes more dependent upon food sources of antioxidants.

Antioxidants such as vitamin E and vitamin C have been used widely in clinical practice to protect the body from harmful free radicals. Other families of antioxidants with more potent free radical scavenging capacities, such as polyphenols, might also be effective for protecting the cardiovascular system. Indeed, the consumption of red wine or pomegranate juice polyphenols by mice as well as by humans has significantly inhibited oxidative stress, atherogenesis and atherosclerotic lesion development.

The pomegranate was recently chosen as the logo for the Millennium Festival of Medicine, mainly because of its medicinal properties as described by all major religions and by folk medicine (11). Pomegranate juice (PJ) possesses impressive antioxidative properties due to its high flavonoids content, mainly the water soluble tannins and proanthocyanins. We have recently shown the antioxidative and anti-atherogenic characteristics of PJ consumption in atherosclerotic apolipoprotein E deficient)(E°) mice. In healthy humans, PJ consumption also demonstrated potent antioxidative capabilities against lipoprotein oxidation, and also increased PON 1 activity and improved serum total antioxidant status.

Studies have shown that pomegranate juice has more polyphenol antioxidants than any other drink, such as red wine, green tea, blueberry juice, cranberry juice and orange juice. Currently, the two common ways of consuming pomegranates are by eating the fleshy arils of the pomegranate and by drinking the juice obtained from the arils.

Oxidative tissue injury occurs when the oxidative burden of the body exceeds its antioxidant capacity. The mechanism of oxidative injury is thought to involve lipid peroxidation, protein oxidation, DNA oxidation, decreased synthesis and bioavailability of endothelial (e) and neuronal (n) nitric oxide (NO), and the up-regulation of proinflammatory cytokines, growth factors and tissue specific receptors. Oxidative injury is known to alter tissue structure and function in many organs, including the heart, blood vessels, lung, kidney and brain. The role of oxidative stress in erectile dysfunction, however, has not been thoroughly investigated.

BRIEF SUMMARY OF THE INVENTION

Methods are provided for producing an extract containing phytochemicals from pomegranate solids. The pomegranate solids are anyone or more of the group consisting of the pericarp, inner membrane and seeds. The extract produced differs from commercially-available pomegranate juice in that the extract is substantially derived from the pomegranate solids, whereas pomegranate juice is substantially derived from the sweet, fleshy arils.

In one preferred embodiment, the method includes the following steps. Any one or a combination of the pericarp, inner membrane and seeds are selected and a mixture is formed comprising the pomegranate solids and an aqueous solution. The mixture is then heated to about 60° F. to 210° F., preferably of about 85° F. to 185° F. and optimally of about 110° F. to 160° F. Enzymes are added to the mixture in an amount sufficient to at least partially degrade the pomegranate solids. Heating liberates phytochemicals from the plant tissues and/or cells. Once liberated, the phytochemicals may react and/or polymerize to create new phytochemical compounds or reaction products. The residual insoluble solid materials are removed from the mixture to provide an extract containing phytochemicals.

In another preferred embodiment, extracts containing phytochemicals from a pomegranate are provided. Such extracts are characterized by a significantly higher total polyphenol content, particularly of the high molecular weight polyphenol (e.g., punicalagin), than is found in pomegranate juice. Such extracts may be obtained from the methods disclosed herein.

In a further preferred embodiment, food products and beverages are provided comprising the extract containing phytochemicals from a pomegranate.

In yet a further preferred embodiment, compositions comprising the extract containing phytochemicals from a pomegranate are provided. Such compositions may be in form of tablets, suspensions, implants, solutions, emulsions, capsules, powders, syrups, liquid compositions, ointments, lotions, creams, pastes, and gels. Such compositions may also be in form of pharmaceutical preparations, nutritional supplements, vitamin supplements, food additives, and food supplements.

In a further preferred embodiment, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract.

In another preferred embodiment, methods are provided for preventing or ameliorating disease conditions in a subject by administering to the subject an effective amount of the composition suitable for use as a pharmaceutical or nutritional preparation. Such disease conditions include polyphenol mediated diseases and cancer. Examples of polyphenol-mediated diseases include circulatory disorders such as hypertension and coronary artery disease, erectile dysfunction, lung disorders such as asthma, cancers of various types, inflammatory conditions, certain liver conditions, diabetes, mood disorders, eye disorders such as cataracts, weak eyesight due to aging, macular degeneration, and other age-related disorders, such as Alzheimer's disease and dementia.

A further aspect of the present invention provides a method of decreasing the incidence of stroke and heart attack in a subject. The method comprises the step of administering to the subject a composition comprising a therapeutically effective amount of an extract from pomegranate. According to the embodiments of the present invention, the stroke or the heart attack is associated with artery arteriosclerotic diseases, including but not limited to, coronary artery arteriosclerosis and carotid artery stenosis, diabetes, high blood pressure, and peripheral vascular disease.

In yet another preferred embodiment, methods are provided for treating a subject with arteriogenic erectile dysfunction using antioxidant therapy from dietary products such as pomegranate juice and extracts thereof as a prophylactic tool for preserving erectile tissue function and preventing cavernous fibrosis in arteriogenic ED, the methods comprising selecting a subject having arteriogenic ED and administering to the subject an effective amount of a composition containing the extract.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications and equivalents thereof. The invention is defined in its fullest scope in the appended claims and is described below in its preferred embodiments.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

Figure 1:
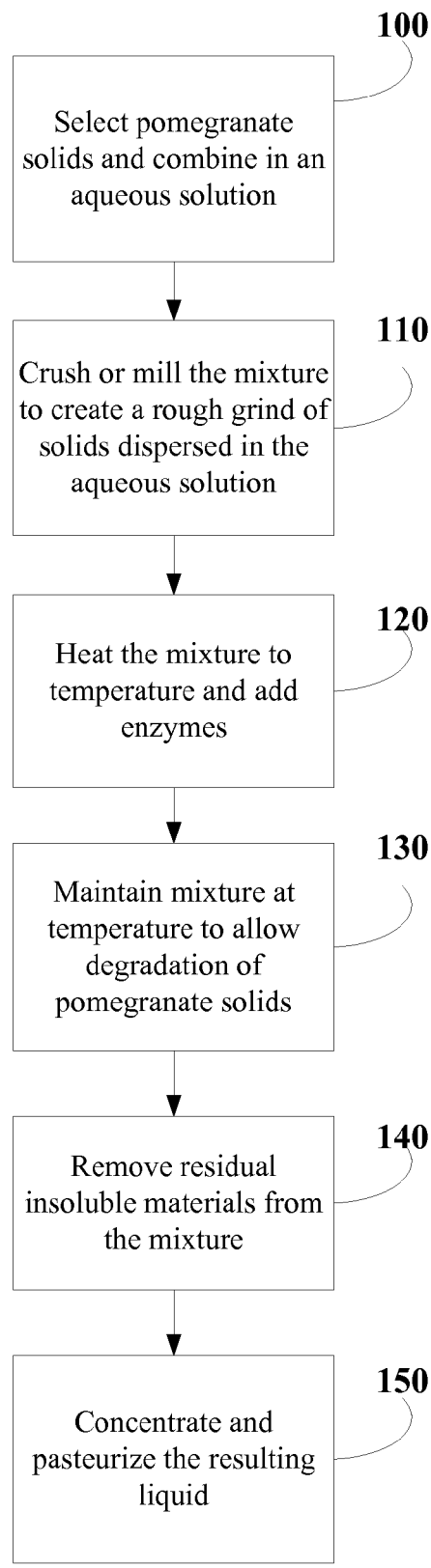
FIG. 1 illustrates a process flow of one or more methods of making the extract of the invention.

As used herein, the term "phytochemicals" refers collectively to compounds which are naturally-occurring in the pomegranate and to reaction products and metabolites of these compounds, which are considered to have a beneficial effect on the human health. Examples of such phytochemicals include, but are not limited to polyphenols, estrogens and phytoestrogens.

As used herein, the term "polyphenols" refers generally to a family of naturally-occurring compounds in the pomegranate and includes phenols and polyphenols. Phenols are a class of chemical compounds consisting of a single phenol unit in their structure. Although similar to alcohols, phenols have unique properties including relatively higher acidities due to the aromatic ring tightly coupled to the oxygen and a relatively loose bond between the oxygen and the hydrogen. Examples of phenolic compounds within this group include ellagic acid and gallic acid. Polyphenols are a group of compounds, characterized by the presence of more than one phenolic group. Polyphenols include tannins (e.g., ellagitannins and gallotannins), flavonoids (e.g., anthocyanins and isoflavones) and stilbenes (e.g., resveratrol).

As used herein, the term "pomegranate juice" refers to the juice that is substantially obtained from the arils of the pomegranate.

As used herein, the term "pomegranate solids" refers to anyone or a combination of the pericarp, the inner membrane and seeds of a pomegranate.

The term "dosage unit" as used herein refers to physically discrete units suitable as unitary dosages for animals, each unit containing a predetermined quantity of active material calculated to produce the desired therapeutic effect in association with the required diluents, e.g., a carrier or vehicle. The specifications for the unit dose of this invention are dictated by and are directly dependent on (a) the unique characteristics of the active material and (b) the limitations inherent in the art of compounding such active material for therapeutic use in animals.

The term "therapeutically effective amount" as used herein means that the amount of the extract of the present invention contained in the composition administered is of sufficient quantity to achieve the intended purpose, such as, in this case, as a prophylactic tool for preserving erectile tissue function and preventing cavernous fibrosis in arteriogenic ED in a subject.

Benefits of Pomegranate Extract

The present invention is based on the unexpected discovery that pomegranate juice consumption by a subject with arteriogenic erectile dysfunction (ED) may cause regression of the size of atherosclerotic lesions. Prior to the present invention, it has been observed that pomegranate juice consumption by rabbits may have a prophylactic affect for preventing smooth muscle dysfunction and fibrosis in ED.

Accordingly, one aspect of the present invention provides a method for treating a subject with arteriogenic ED. The method comprises the step of administering to the subject a composition comprising a therapeutically effective amount of an extract from pomegranate fruit. The extract of pomegranate may be a juice extract of pomegranate, an extract from inner or outer peel of pomegranate, or the mixture thereof.

It has been surprisingly discovered that extracts obtained from the pomegranate solids, in accordance with the methods disclosed herein, have substantially higher total polyphenol content than is found in the juice from the pomegranate arils. This is particularly true with respect to the higher molecular weight polyphenols and, in particular, punicalagin.

Punicalagin is a powerful antioxidant, protecting cardiovascular function and accurate cellular replication. Thus, punicalagin is responsible, in part, for the high antioxidant activity of the extract. While the antioxidant and other beneficial health effects of the extract are due to the presence of polyphenols, the presence of other phytochemical compounds in the extract, or the synergistic effect of these phytochemicals, may also be responsible for the anti-oxidant and other beneficial health effects of the extract.

In addition to punicalagin, other high molecular weight polyphenols have been characterized in the extract of pomegranate solids. These high molecular weight polyphenols include ellagitannin and other hydrolysable tannins, such as punicacortein A, punicalin, pedunculagin, and gallotanin dimers and trimers.

Moreover, a large number of anthocyanins have been characterized in the extract of the pomegranate solids. Examples of the anthocyanins include pelargonidin 3-glucoside, cyaniding 3-glucoside, delphinidin 3-glucoside, pelargonidin 3,5-diglucoside, cyaniding 3,5-diglucoside, and delphinidin 3,5-diglucoside. Although these anthocyanins have been characterized in both the pomegranate juice and the extract, these lower molecular weight polyphenols comprise a higher proportion of the total polyphenol content in pomegranate juice (approximately 50%) than in the extract.

Various Methods of Making Pomegranate Extract

Accordingly, methods are provided for producing an extract containing phytochemicals from pomegranate solids. The extract produced from the methods disclosed herein differ from the commercially-available pomegranate juice in that the extract is substantially derived from the pomegranate solids, whereas pomegranate juice is substantially derived from the sweet, fleshy arils that surround the pomegranate seed. The extract is characterized as containing polyphenols and, particularly, high molecular weight polyphenols, such as punicalagin.

FIG. 1 illustrates a method of making the extract in one or more embodiments, the method comprises at 100 selecting any one or a combination of pomegranate solids selected from the group consisting of the pericarp, inner membrane and seeds and creating a mixture comprising the pomegranate solids in an aqueous solution. In a preferred embodiment, the mixture of the pomegranate solids is created by adding water in an amount that is about 20-80% w/v, and more preferably about 50% w/v, of the pomegranate solids. At 110, the mixture is preferably crushed or milled to create a rough grind of pomegranate solids dispersed in the aqueous solution.

At 120, the mixture may then be heated to a temperature of about 60° F. to 210° F., preferably of about 85° F. to 185° F. and optimally of about 110° F. to 160° F. The temperature to which the mixture is heated depends upon the selection of enzymes, or combination of enzymes, that is added to the mixture. Preferably, the mixture is heated to a temperature that permits the maximum catalysis of the enzyme or combination of enzymes.

Alternatively, enzymes may be added before the mixture is heated. Thus, the order of the steps of heating the mixture and adding the enzymes is not critical, so long as the mixture is heated to a temperature that permits the enzymes to at least partially degrade the pomegranate solids. Heating will liberate the phytochemicals, which may then react and/or polymerize to create new phytochemical compounds or reaction products.

Enzymes suitable for use in accordance with this embodiment include those which are capable of at least partially degrading the plant tissue or cells to liberate the phytochemicals from the pomegranate solids. Such enzymes include anyone or a combination of pectinase, cellulase, hemicellulase, amylase, arabanase, and other hydrolyzing enzymes, to name a few. The enzymes added to the mixture may be naturally-occurring or synthetic. They may be derived from any one or a combination of sources, such as animal, plant, fungal, and bacterial sources. The amount of the enzyme or combination of enzymes added to the mixture depends on the temperature of the mixture and the amount of pomegranate solids present in the mixture.

At 130, after enzymes are added, the mixture is maintained at a temperature for a time sufficient to allow at least partial degradation of the pomegranate solids. The temperature and length of time required depends on the type of enzymes added to the mixture, the rate of enzyme catalysis and the amount of the pomegranate solids contained in the mixture.

Thus, in one preferred embodiment, a combination of pectinase, cellulase and hemicellulase enzymes are added to the mixture, which is heated to a temperature of about 60° F. to 210° F., preferably about 110° F. to 160° F., and optimally of about 120° F. The mixture is maintained at these temperatures, preferably with agitation or stirring, for about 45-195 minutes, preferably for about 45-75 minutes, and optimally for about 60 minutes.

At 140, after the enzymes have at least partially degraded the pomegranate solids, the residual insoluble solid materials are removed from the mixture. Optionally, a clarification agent, such as bentonite, may be added before the step of removing the residual insoluble materials from the mixture. The removal of residual insoluble materials from the mixture may be accomplished by filtration, centrifugation, chromatographic techniques, and other techniques. Filtration techniques suitable for the practice of the methods disclosed herein include micro-filtration at a molecular weight cut-off of at least 1,000 Da, preferably of about 4,500 Da, and optimally of about 5,500 Da.

At 150, the resulting liquid extract may be concentrated in an evaporator under vacuum to about 50-90 Brix (Bx), preferably to about 60-80 Bx, and optimally to about 70 Bx, and pasteurized at a temperature and for a length of time sufficient to kill microorganisms that could cause disease, spoilage or undesired fermentation. In one preferred embodiment, the extract may be pasteurized at a temperature of about 140° F.-280° F., preferably of about 195° F.-240° F., and optimally of about 205° F. The pasteurization may also denature the remaining enzymes that were added to the mixture.

Alternative Methods of Making Pomegranate Extract

For the purpose of the present invention, in one or more embodiments an extract from pomegranate may also be an extract from the whole pomegranate fruit or from any constituents of pomegranate fruit. Examples of constituents of pomegranate fruit that may be used to make the extract of the present invention include, but are not limited to, juice, seed, and the inner and outer peel of pomegranate fruit. In one embodiment of the present invention, the extract is the juice extract of whole pomegranate fruit. In another embodiment of the present invention, the extract is from the inner or outer peel of pomegranate fruit. In a further embodiment of the present invention, the extract may be a mixture of two or more extracts of the whole pomegranate or any constituents of pomegranate.

Figure 2:
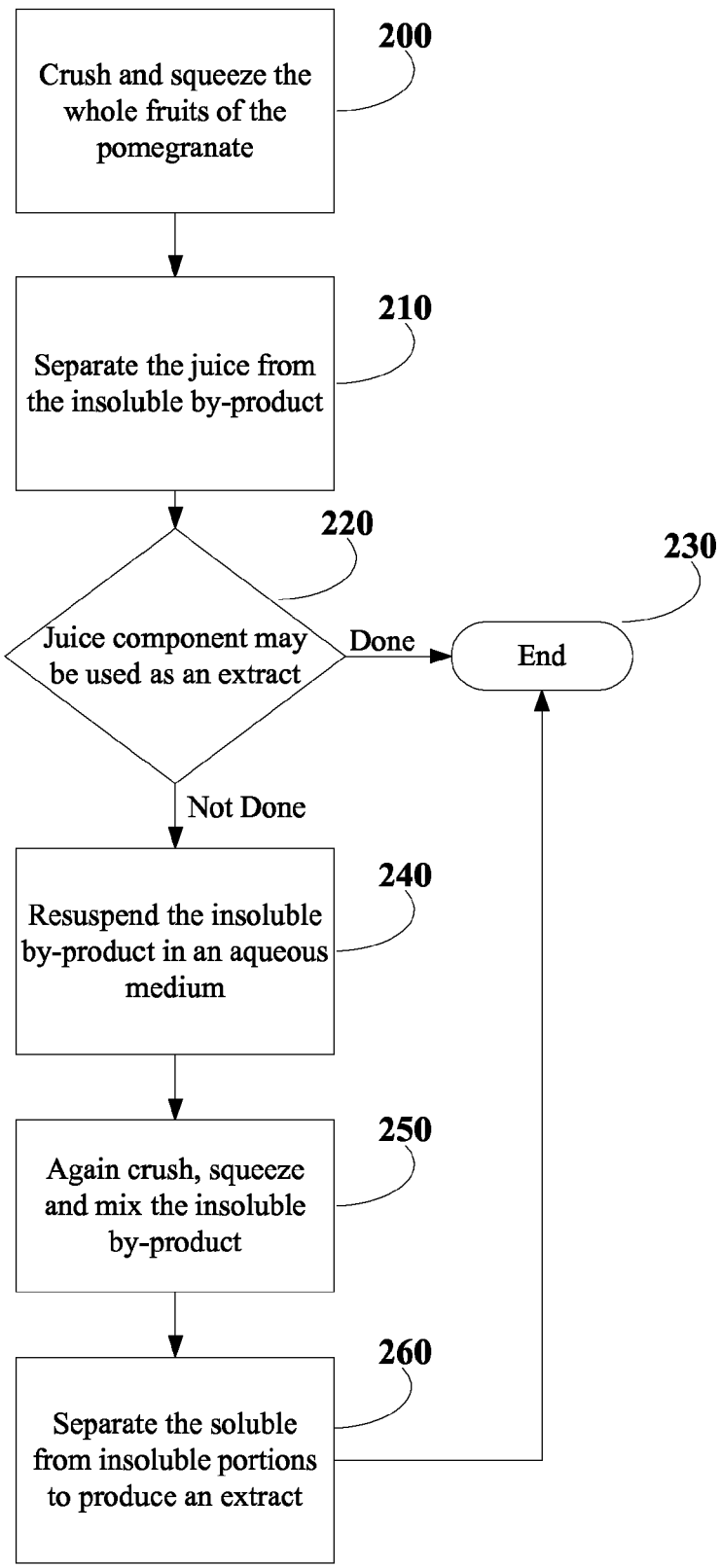
FIG. 2 illustrates an alternative process flow of one or more methods of making the extract of the invention.

FIG. 2 illustrates another method of making the extract in accordance with one embodiment of the present invention, the extract of the present invention may be prepared by a process including the steps of: at 200, crushing and squeezing the whole fruits of the pomegranate, including the inner and outer peels and the seeds, to yield a juice component and a first insoluble by-product component, and at 210, separating the juice component from the insoluble by-product component. At 220, the juice component may be used as a juice extract of the present invention. Alternatively, at 240 the insoluble by-product component may be resuspended in an aqueous medium, such as, but not limited to, water or alcohol, and at 250 the insoluble by-product component may be further crushed, squeezed, and mixed to yield a soluble portion and a second insoluble by-product component. At 260, then, the soluble portion may be separated from the second insoluble by product component to produce a second form of the extract of the constituents of the present invention. Alternatively, the soluble portion may be combined with the juice extract to produce a third form of extract of the present invention.

In one embodiment of the present invention, the whole fruit of the pomegranate may be enzymatically treated to improve extraction and filtration. For example, pectinase may be used to treat the whole fruit to prevent the formation of pectin gels. Other enzymes known in the art may also be used as long as they can improve extraction and filtration of the extract of the present invention.

The extract of pomegranate of the present invention may be in a liquid or solid form. In accordance with one embodiment of the present invention, a solid form of the extract may be made by lyophilizing the liquid extract of the present invention. Alternatively, the constituents of the pomegranate, such as seeds, inner or outer peels, or any insoluble by-product component discussed above, may be processed directly to form the solid form of the extract of the present invention. For example, the constituents of the pomegranate may be dried, and processed into powder or pill forms to be used directly as the solid form of the extract of the present invention.

Compositions of the present invention may be a variety of kinds, including, but not limited to, nutritional supplements, pharmaceutical preparations, vitamin supplements, food additives, or foods supplements. Compositions of the present invention may be in convenient dosage forms, including, but not limited to, tablets, suspensions, implants, solutions, emulsions, capsules, powders, syrups, liquid compositions, ointments, lotions, creams, pastes, gels, or the like.

Compositions of the present invention may include a carrier. Depending on the kind of compositions of the present invention, a carrier may be a dietary suitable carrier or a pharmaceutically acceptable carrier, as long as it is compatible with the particular kind of compositions of the present invention. Examples of a dietary suitable carrier include, but are not limited to, dietary suitable excipients, diluents, and carriers. Examples of a pharmaceutically acceptable carrier include, but are not limited to, biocompatible vehicles, adjuvants, additives, and diluents to achieve a composition usable as a dosage form. As used herein, the terms "pharmaceutically acceptable," "physiologically tolerable," and grammatical variations thereof, as they refer to compositions, carriers, diluents, and reagents, are used interchangeably and represent that the materials are capable of administration to or upon a mammal without the production of undesirable physiological effects.

The compositions of the present invention may be used alone or in combination with other biologically active ingredients. A composition of the present invention, alone or in combination with other active ingredients, may be administered to a subject in a single dose or multiple doses over a period of time, generally by oral administration. Various administration patterns will be apparent to those skilled in the art. The dosage ranges for the administration of the compositions of the present invention are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

In one embodiment of the present invention, a composition contains the extract of pomegranate in a dosage unit in an amount that contains at least 30 to 3000 µmols per dosage unit of polyphenols. For the purpose of the present invention, polyphenols are those naturally present in the extract of pomegranate. It should be appreciated that polyphenols are used herein as a measurement marker for the amount of extract that needs to be used in each dosage unit. They are not used herein as an indication that they are the active, or the only active, ingredients of the extract. In fact, it is possible that something else, or the synergy of polyphenols and other components of an extract of the present invention, may be responsible for the activities of the extract.

Additional Methods of Making Extracts

In one or more embodiments, a concentrate may be prepared from fresh pomegranates crushed in a champagne press. Because whole fruit is crushed, beneficial antioxidants from the peel and membranes are added to those already found in the juice. After crushing, the juice is enzymatically treated with pectinase, filtered, concentrated and stored at −18° C.

Finally, all the methods of making described above may be used or may be combined to produce an extract of PJ, PJ solids, or a combination thereof. The preceding description of methods of making PJ extract are intended to provide examples and not limitations on the methods of making the extract of the invention.

Properties of the Extracts

In one embodiment of the present invention, a composition contains the extract of pomegranate in a dosage unit in an amount that contains at least 30 to 3000 µmols per dosage unit of polyphenols. For the purpose of the present invention, polyphenols are those naturally present in the extract of pomegranate. It should be appreciated that polyphenols are used herein as a measurement marker for the amount of extract that needs to be used in each dosage unit. They are not used herein as an indication that they are the active, or the only active, ingredients of the extract. In fact, it is possible that something else, or the synergy of polyphenols and other components of an extract of the present invention, may be responsible for the activities of the extract.

Forms of the Extracts

In another preferred embodiment, extracts containing phytochemicals from a pomegranate are provided. Such extracts are characterized by a significantly higher total polyphenol content, particularly of the high molecular weight polyphenol (e.g., punicalagin), than is found in pomegranate juice. Such extracts may be obtained from the methods disclosed herein. In a further preferred embodiment, extracts containing phytochemicals, polyphenols, punicalagin, punicalin, ellagic acid, and metabolite thereof are provided.

In yet another preferred embodiment, food products and beverages are provided comprising the extract containing phytochemicals from a pomegranate. For example, due to the significantly higher total polyphenol content in the extract, an 8 oz sports beverage containing 0.33 oz of the extract may be formulated to deliver the same total polyphenols as a 20 oz single-strength pomegranate juice. The polyphenol content of pomegranate juice is approximately about 1 to 2.25 mg/mL and the amount of polyphenols present in 20 oz of juice is approximately 567 to 1,256 mg. In contrast, the extract may contain a polyphenol content of about 60 to 120 mg/mL, depending on the method employed. Thus only 0.33 oz of the 70 Bx extract would be needed to provide the equivalent amount of polyphenols in 20 oz of the juice.

In a further preferred embodiment, compositions comprising the extract containing phytochemicals from a pomegranate are provided. The extract of pomegranate of the present invention may be in a liquid or solid form. The compositions may be formulated in the form of tablets, suspensions, implants, solutions, emulsions, capsules, powders, syrups, liquid compositions, ointments, lotions, creams, pastes, gels, and the like.

In accordance with one embodiment of the present invention, a solid form of the extract may be made by lyophilizing the liquid extract of the present invention. Alternatively, the constituents of the pomegranate, such as seeds, inner or outer peels, or any insoluble portion discussed above, may be processed directly to form the solid form of the extract of the present invention. For example, the constituents of the pomegranate may be dried, and processed into powder or pill forms to be used directly as the solid form of the extract of the present invention.

Compositions of the present invention may be a variety of kinds, including, but not limited to, nutritional supplements, pharmaceutical preparations, vitamin supplements, food additives, or foods supplements. Compositions of the present invention may be in convenient dosage forms, including, but not limited to, tablets, suspensions, implants, solutions, emulsions, capsules, powders, syrups, liquid compositions, ointments, lotions, creams, pastes, gels, or the like.

Compositions of the present invention may include a carrier. Depending on the kind of compositions of the present invention, a carrier may be a dietary suitable carrier or a pharmaceutically acceptable carrier, as long as it is compatible with the particular kind of compositions of the present invention. Examples of a dietary suitable carrier include, but are not limited to, dietary suitable excipients, diluents, and carriers. Examples of a pharmaceutically acceptable carrier include, but are not limited to, biocompatible vehicles, adjuvants, additives, and diluents to achieve a composition usable as a dosage form.

As used herein, the terms "pharmaceutically acceptable," "physiologically tolerable," and grammatical variations thereof, as they refer to compositions, carriers, diluents, and reagents, are used interchangeably and represent that the materials are capable of administration to or upon a mammal without the production of undesirable physiological effects.

The compositions of the present invention may be used alone or in combination with other biologically active ingredients. A composition of the present invention, alone or in combination with other active ingredients, may be administered to a subject in a single dose or multiple doses over a period of time, generally by oral administration. Various administration patterns will be apparent to those skilled in the art. The dosage ranges for the administration of the compositions of the present invention are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

The compositions may also be prepared in forms suitable for use as pharmaceutical preparations, nutritional supplements, vitamin supplements, food supplements, and food additives for improving the health of a subject comprising obtaining an extract containing phytochemicals from a pomegranate and admixing an effective amount of the extract. As such, the compositions may optionally include a suitable carrier or excipient.

Suitable carriers or excipients are inert ingredients and include, by way of example, fillers, e.g. sugars such as lactose, glucose or sucrose, sugar alcohols such as mannitol, sorbitol or xylitol, starch such as wheat, corn or potato starch, modified starch or sodium starch glycolate, lubricants such as talc, magnesium stearate, calcium stearate, colloidal silica or stearic acid, and binders such as polyvinylpyrrolidone, cellulose derivatives, carboxymethyl cellulose, hydroxylpropyl cellulose, hydroxypropylmethyl cellulose, methyl cellulose or gelatin.

Methods of Treating: Dosage and Administration

In another preferred embodiment, methods are provided for treating a polyphenol-mediated condition in a subject comprising selecting a subject having a polyphenol-mediated condition and administering to the subject an effective amount of the composition comprising the extract.

Conventional procedures for preparing such compositions in appropriate dosage forms of the extract may be utilized. Such compositions may be administered orally or parenterally employing liquid form preparations containing the extract.

The compositions may be administered orally, in appropriate dosage units of the extract in a pharmaceutically acceptable carrier or excipient. Thus, the compositions may be formulated into solid or liquid preparations, such as capsules, pills, tablets, powders, solutions, suspension, or emulsions and may be prepared according to methods known in the art for the manufacture of such compositions. The solid unit dosage forms may be in form of a hard or soft shelled gelatin capsule containing the extract and a suitable carrier or excipient.

The composition may also be administered parenterally as injectable dosages in a physiologically acceptable carrier. Parenteral administration may be subcutaneous, intravenous, intramuscular, or interperitoneally.

The effective amount of a composition is the amount or dosage unit of the extract sufficient to achieve the intended beneficial health results. Accordingly, the effective amount of the composition to be administered depends on considerations such as the dosage unit employed, the mode of administration, the period of treatment, the age, sex and weight of the person treated and the nature and extent of the condition treated. The effective amount can readily be determined based upon standard techniques known to evaluate whether the intended effect of the composition has been achieved, by standard toxicity tests and by standard pharmacological assays.

In a further preferred embodiment, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract, for example the lower molecular weight polyphenols (e.g., anthocyanins) which is present in greater quantities in the pomegranate juice and the higher molecular weight polyphenols (e.g., punicalagin, punicalin, ellagic acid glycosides, ellagic acid polyphenols, ellagitannin and other hydrolysable tannins, such as punicacortein A, punicalin, pedunculagin, and gallotanin dimers and trimers).

In yet a further preferred embodiment, methods are provided for ameliorating disease conditions in a subject by administering to the subject an effective amount of the composition suitable for use as a pharmaceutical or nutritional preparation. Such disease conditions include polyphenol mediated diseases such as arteriogenic ED.

Polyphenols and countless other phytochemicals in the extract are necessary for the various organs and tissues and for the proper functioning of the human body. Accordingly, many disease conditions may be prevented or ameliorated by the administration of polyphenols to subjects with polyphenol mediated diseases. These polyphenol-mediated diseases include circulatory disorders such as hypertension and coronary artery disease, erectile dysfunction, lung disorders such as asthma, cancers of various types, inflammatory conditions, certain liver conditions, diabetes, mood disorders, eye disorders such as cataracts, weak eyesight due to aging, macular degeneration, and other age-related disorders, such as Alzheimer's disease and dementia.

Results of Treating with Extract

It is an unexpected discovery of the present invention that pomegranate juice consumption can cause regression in the atherosclerotic lesions such as those related to arteriogenic ED, as well as acting as an antioxidant therapy for the oxidative stress that may be of great importance in the pathophysiology of arteriogenic ED. Therefore, it is believed that pomegranate juice consumption may act as a prophylactic tool for preventing smooth muscle dysfunction and fibrosis in ED.

Further, various pharmaceuticals are also known to treat arteriogenic ED. Therefore, it would be a logical extension of treating conditions known as causes of arteriogenic ED with the various extracts of the invention to combine the extracts with such pharmaceuticals to achieve an even better result.

EXAMPLES

The following examples further illustrate the embodiments disclosed herein. These examples are provided only for purpose of illustrating the preferred embodiments of the invention and do not limit the invention in any manner.

Example 1

Production of Liquid Extract from Pomegranate Solids

The starting material for the production of the extract is the pomegranate solids, which generally comprise the pericarp, the inner membrane and seeds of the pomegranate. The pomegranate solids were obtained and collected after the primary juice from the arils had been substantially expelled or otherwise removed from the pomegranate by pressing, crushing, or other methods known to the art for extracting pomegranate juice.

The pomegranate solids were then transferred to three Reitz Mills with ⅜-inch screens. The material was milled to a fine puree and heated to approximately 125° F. This step, coupled with the following enzyme addition, assisted in breaking down the colloidal structure of the remaining pomegranate solids, thereby releasing the remaining soluble solids.

The mixture was heated to a temperature of about 125° F. for two hours. Three enzymes were added to the mixture: pectinase (Rohapect® DA6L), cellulase/pectinase (Rohapect® CL), and hemi-cellulase/pectinase (Rohapect® B1L). These enzymes were used to liberate the remaining pomegranate soluble solids, such as sugars, minerals, anthocyanins, and remaining polyphenols.

The mixture was then pumped from the extraction plant to the primary processing plant where it was held in the mash treatment tanks for approximately one hour. After one hour, 50-100 pounds of bentonite in a 125 gallon water slurry, per 8,000 gallons of the mixture, was added for protein removal. The treated mixture was then passed through a Westphalia 755 Decanter for removal of solids. The residual insoluble material was discharged as waste.

The remaining liquid extract was processed in a Schmidt evaporator. In this step, the extract was stripped and rectified. In addition, the liquid extract was pre-concentrated and then pasteurized to 205° F. for 45 seconds. The liquid extract then exited the evaporator and was filtered on Koch Micro-Filtration membranes at a 4,500 Da molecular weight cut-off for liquid extract soluble solids.

The liquid extract then re-entered the evaporator for final concentration. Initial heat on this step was about 185-195° F. At about 70 Bx, the liquid extract was cooled to less than about 45° F. and pumped to the concentrate batching room where it was blended and standardized.

Example 2

Comparison of Polyphenol Content in Extracts of Pomegranate Solids and in Pomegranate Juice The concentrations of punicalagin, punicalin, ellagic acid glycosides, and ellagic acid polyphenols in the pomegranate juice and the pomegranate extract were analyzed and compared in a University study.

All samples (50 mL injection volume) were filtered (0.22 mm) and analyzed on a Novapak (Waters Corp.) C-18 column, 150×3.9 mm i.d., 5 mm. The mobile phase, solvent A (2% $CH_3COOH/H_2O$) and solvent B (2% aqueous $CH_3COOH/CH_3OH$) was used under linear gradient conditions starting with 99% solvent A in solvent B to 40% solvent A in solvent B over 40 minutes, hold time, 5 minutes with a flow rate of 1 mL/min. All compounds were detected at 254 nm, and at 378 nm (punicalagins) and 366 (ellagic acid) for quantification.

Table 1 shows a side-by-side comparison of the concentration of the polyphenols punicalagins, punicalin, ellagic acid glycosides, and ellagic acid in the pomegranate extract and the pomegranate juice.

TABLE 1

| Compound Name | Pomegranate Extract Concentration (mg/ml) | Pomegranate Juice Concentration (mg/ml) |
|---|---|---|
| Punicalagin (β isomer) | 4.79 | 0.02 |
| Punicalagin (α isomer) | 21.80 | 0.15 |
| Punicalin | 3.62 | NA |
| Ellagic Acid Glycosides | 19.65 | 0.33 |
| Ellagic Acid | 18 | 0.74 |
| Total | 67.86 | 1.24 |

Although other polyphenols are present in both the pomegranate extract and juice, and this example highlights the unexpected and surprising results in that significantly higher concentrations of polyphenols, particularly of punicalagin, are present in the pomegranate extract than in the pomegranate juice. Table 1 shows a total punicalagin (for both α- and β-isomers) concentration for the pomegranate extract that is over 26-fold greater than for the pomegranate juice.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of treating a subject with erectile dysfunction, said method comprising the steps of administering to said subject a composition comprising a therapeutically effective amount of an extract from pomegranate, wherein said extract is prepared by a process comprising the steps of:
   providing one or more pomegranate solids selected from the group consisting of pericarp, inner membrane and seeds;
   creating a mixture comprising said pomegranate solids in an aqueous solution;
   crushing said mixture to create a rough grind of pomegranate solids dispersed in said aqueous solution;
   adding enzymes to said mixture;
   heating said mixture to a temperature that permits catalysis of said enzymes;
   maintaining said mixture at said temperature for a time sufficient to allow at least partial degradation of said pomegranate solids;
   removing residual insoluble solid material from said mixture after said partial degradation has occurred to produce a liquid extract;
   concentrating said liquid extract in an evaporator under vacuum; and
   pasteurizing said liquid extract.

2. The method of claim 1 further comprising: wherein said heating of said mixture is to a temperature of about 60° F. to 210° F.

3. The method of claim 1 further comprising: wherein said aqueous solution comprises water in amount that is about 20-80% w/v of said pomegranate solids.

4. The method of claim 1 further comprising: adding a clarification agent before removing said residual insoluble material from said mixture.

5. The method of claim 1 wherein said enzymes comprise at least one of: pectinase, cellulose, hemicellulose, amylase, and arabanase.

6. The method of claim 1 wherein said enzymes are synthetic.

7. The method of claim 1 wherein enzymes comprise a mixture of pectinase, cellulose and hemicellulose enzymes; and wherein said mixture is heated to a temperature of about 60° F. to 210° F.

8. The method of claim 1 further comprising: stirring said mixture at said temperature for about 45-195 minutes.

9. The method of claim 1 further comprising: pasteurizing said extract at a temperature of about 140° F.-280° F.

10. The method of claim 1 wherein said residual insoluble material is removed from said mixture by filtration, centrifugation, or chromatographic techniques.

11. The method of claim 10 wherein said filtration techniques include micro-filtration at a molecular weight cut-off of at least 1,000 Da.

* * * * *